United States Patent [19]

Andrews

[11] 4,276,219
[45] Jun. 30, 1981

[54] 5-KETO-L-ASCORBIC ACID-5,5-DIMETHYL KETAL, DERIVATIVES THEREOF AND ITS USE AS AN ANTIOXIDANT AND INTERMEDIATE

[75] Inventor: Glenn C. Andrews, Waterford, Conn.

[73] Assignee: Pfizer Inc., New York, N.Y.

[21] Appl. No.: 59,417

[22] Filed: Jul. 20, 1979

[51] Int. Cl.$^3$ .......................................... C07D 307/62
[52] U.S. Cl. ................................................. 260/343.7
[58] Field of Search ..................................... 260/343.7

[56] References Cited

U.S. PATENT DOCUMENTS

| | | | |
|---|---|---|---|
| 4,159,990 | 7/1979 | Andrews | 260/343.7 |
| 4,180,511 | 12/1979 | Crawford | 260/343.7 |

OTHER PUBLICATIONS

E.R.H. Walker, Chem. Soc. Reviews (1976) vol. 5, pp. 26, 27, 31, 49, 50.
N. Umino et al., Tetrahedron Letters, No. 10 (1976) pp. 763–766.

*Primary Examiner*—Norma S. Milestone
*Attorney, Agent, or Firm*—Francis X. Murphy; Charles J. Knuth; Albert E. Frost

[57] ABSTRACT

5-Keto-L-ascorbic acid-5,5-dimethyl ketal, alkali metal and alkaline earth metal salts thereof; process for the preparation thereof; its use as an antioxidant and intermediate for production of 5-keto-L-ascorbic acid and L-ascorbic acid. 5-Keto-L-ascorbic acid and its 5,5-dimethyl ketal exhibit antiscorbutic activity.

1 Claim, No Drawings

5-KETO-L-ASCORBIC ACID-5,5-DIMETHYL KETAL, DERIVATIVES THEREOF AND ITS USE AS AN ANTIOXIDANT AND INTERMEDIATE

BACKGROUND OF THE INVENTION

1. Field of the Invention

This invention relates to 5-keto-L-ascorbic acid-5,5-dimethyl ketal and to a process for its preparation by the reaction of methyl 2,5-diketogluconate-5,5-dimethyl ketal with an inorganic base in an alcohol or aqueous solvent system followed by neutralization of the 5-keto-L-ascorbic acid-5,5-dimethyl ketal inorganic salt thus produced. The 5,5-dimethyl ketal of 5-keto-L-ascorbic acid is an effective antioxidant, an antiscorbutic agent, and an intermediate for production of 5-keto-L-ascorbic acid, also an antiscorbutic agent, and L-ascorbic acid.

2. Description of the Prior Art

Finkle et al., Biochim. Biophys. Acta, 38, 332–339 (1960), proposed 5-keto-L-ascorbic acid as an intermediate in the biosynthesis of ascorbic acid in plants. However, no enabling disclosure as to its preparation is given, and no evidence has been found to data to support this proposal.

3. Summary of the Invention

This invention relates to 5-keto-L-ascorbic acid-5,5-dimethyl ketal and to a method for its preparation which comprises reacting methyl 2,5-diketogluconate-5,5-dimethyl ketal with an inorganic base in a solvent selected from the group consisting of water, alcohols having from one to four carbon atoms and mixtures of said solvents at a temperature of from about 20° C. to the reflux temperature of the solvent. The inorganic salt of 5-keto-L-ascorbic acid-5,5-dimethyl ketal thus produced is then neutralized in a liquid medium to produce 5-keto-L-ascorbic acid-5,5-dimethyl ketal which, when treated with a strong acid, produces 5-keto-L-ascorbic acid, a compound embraced within this invention in its keto, hydrated and enol forms. Reduction of 5-keto-L-ascorbic acid with sodium cyanoborohydride or zinc cyanoborohydride in water at pH values of 2.5 to 2 affords L-ascorbic acid.

DETAILED DESCRIPTION OF THE INVENTION

The process of this invention for making 5-keto-L-ascorbic acid comprises reacting methyl 2,5-diketogluconate-5,5-dimethyl ketal (described in Belgian Pat. No. 861,693, granted June 9, 1978) with an inorganic base; e.g., an alkali metal or alkaline earth metal basic salt, representative of which are the bicarbonates, carbonates, hydroxides and alkoxides wherein the alkoxide group has from one to four carbon atoms. The reaction is conducted in a solvent selected from the group consisting of water, alcohols having from one to four carbon atoms and mixtures of said solvents. The favored bases are sodium or potassium methoxide and sodium or potassium hydroxide. Preferred bases are sodium or potassium bicarbonate. The preferred solvent is methanol because of the fact that the 5-keto-L-ascorbic acid-5,5-dimethyl ketal sodium or potassium salt precipitates from the reaction mixture and is readily recovered.

The temperature of the reaction can range from about 0° C. to the reflux temperature of the solvent. There appears to be a relationship between the strength of the base used and the optimum temperature for a given reaction. The stronger bases, such as potassium or sodium methoxide and hydroxide, permit the use of temperatures at the lower range with production of satisfactory yields of the desired ketal. When using a weak base such as sodium or potassium bicarbonate a temperature of at least about 20° C. should be used and desirably a temperature of at least about 40° C. The preferred temperature when using a weak base is the reflux temperature.

The reaction period is, of course, related to the temperature and/or base used. In general, the stronger the base and the higher the temperature, the less time is required for the reaction. In most instances, a reaction period of from about 2 to about 24 hours is used.

The methyl 2,5-diketogluconate-5,5-dimethyl ketal and inorganic base are generally reacted in the ratio of from about 1.0 to about 1.5 equivalent moles of base per equivalent of dimethyl ketal reactant. While the proportion of reactants used is not critical, the use of less than one equivalent of base per equivalent of dimethyl ketal reactant is not desirable since it tends to reduce the yield of desired product. The use of more than 1.5 equivalent moles of base does not appear to improve the yield of the desired product. The preferred procedure comprises reacting equimolar amounts of methyl 2,5-diketogluconate-5,5-dimethyl ketal and sodium bicarbonate in methanol for a period of about 5 hours.

The 5-keto-L-ascorbic acid-5,5-dimethyl ketal salt; e.g., sodium (or potassium) salt, thus produced is then neutralized in liquid medium, e.g. water, to produce 5-keto-L-ascorbic acid-5,5-dimethyl ketal. The nature of the neutralizing agent is not critical. Both inorganic and organic acids having $pK < 2$, such as those enumerated below can be used. Preferred as neutralizing agents are the acid forms of sulfonic acid cation exchange resins. Such neutralizing agents are favored because of the ease with which they can be removed from the neutralizing reaction mixture, thus affording a simple procedure for recovering the desired product.

Suitable cation exchange resins are the sulfonic acid-type which are copolymers of sulfonated polystyrene and divinyl aromatic compounds such as divinylbenzene and divinyl toluene. Such resins are described in U.S. Pat. Nos. 2,579,974; 2,191,853; 2,366,007 and 2,518,420.

The 5-keto-L-ascorbic acid-5,5-dimethyl ketal thus obtained is then treated with a strong acid in the presence of water to produce 5-keto-L-ascorbic acid. The acid reactant can be a strong ($pK < 2$) inorganic or organic acid. Representative of the inorganic acids useful in this step are the mineral acids. Representative of organic acids useful for regenerating the keto function are trifluoroacetic acid, trichloroacetic acid, methanesulfonic acid and p-toluenesulfonic acid. Neutralization of the 5-keto-L-ascorbic acids with alkali metal or alkaline earth metal bases such as are enumerated above affords the corresponding alkali metal or alkaline earth metal salts.

In water, at pH 2–3, 5-keto-L-ascorbic acid exhibits no free carbonyl group in the infrared or by $C^{13}$ nuclear magnetic resonance spectroscopy, suggesting it exists as a fully hydrated 5-keto moiety. The ultraviolet absorption spectrum in water at pH 2.5 exhibits a single maximum at 247 m$\mu$. Thus, in water, 5-keto-L-ascorbic acid exists in the hydrated form to the extent of at least 95%, the remaining 5% or less being the enol form.

Catalytic or chemical reduction of 5-keto-L-ascorbic acid affords L-ascorbic acid. Catalytic reduction can be accomplished using Raney nickel or noble metals at hydrogen pressures ranging from subatmospheric to super-atmospheric pressures. Chemical reduction can be carried out using amine boranes (ammonia, primary or secondary amine boranes), borohydrides of sodium, calcium or zinc, or cyanoborohydrides of sodium or zinc. The use of alkali metal borohydrides, e.g., sodium or potassium borohydride, in strong acid media, e.g. trifluoroacetic acid, permits direct conversion of 5-keto-L-ascorbic acid-5,5-dimethyl ketal to L-ascorbic acid.

Reduction of 5-keto-L-ascorbic acid in water at pH 2.5 with sodium cyanoborohydride afforded a mixture of ascorbic and erythorbic acids in the ratio of about 3:1. Reduction of 5-keto-L-ascorbic acid by means of zinc cyanoborohydride in water at pH 2 afforded a mixture of ascorbic and erythorbic acids of approximately 2:1. The mixtures were totally racemic.

The 5-keto-L-ascorbic acid-5,5-dimethyl ketal and 5-keto-L-ascorbic acid are effective antioxidants as determined in the Schaal oven test at 63° C. in soybean oil ("Handbook of Food Additives," T. E. Furia, Editor, Chemical Rubber Company Press, Cleveland, Ohio, 2nd Ed., p. 201, 1975). Comparison of the antioxidant effectiveness of 5-keto-L-ascorbic acid-5,5-dimethyl ketal with that of related antioxidants is provided below:

| Antioxidant | Days to Peroxide Value of 70 meg/kg of oil |
| --- | --- |
| 0.02% erythorbic acid | 13 |
| 0.02% erythorbyl laurate | 20 |
| 0.02% 5-keto-L-ascorbic acid-5,5-dimethyl ketal | 23 |
| none | 11 |

When intimately mixed; i.e., dissolved in, added as a solution, dispersed as solid particles, with oxidizable substances, especially with deterioration-prone consumables such as food products, edible oils, essential oils, fats, nuts, flavorings, vitamins and pharmaceuticals, 5-keto-L-ascorbic acid-5,5-dimethyl ketal and 5-keto-L-ascorbic acid, and the alkali metal and alkaline earth metal salts thereof, when used at a level of from 10 to 1,000 ppm, based on the weight of the consumable substance, effectively retard their oxidation. The favored amount is from 10 to 200 ppm.

5-Keto-L-ascorbic acid, preferably as the sodium salt, and 5-keto-L-ascorbic acid-5,5-dimethyl ketal are also valuable inhibitors of nitrosamine formation such as occurs in meat products containing nitrite, e.g., frankfurters and bacon. The addition of from about 250 to about 1000 ppm of sodium 5-keto-L-ascorbate or 5-keto-L-ascorbic acid-5,5-dimethyl ketal to the meat prior to or during curing effectively reduces nitrosamine formation. The procedure described by Fiddler et al., J. Ag. Food Chem. 26, 653 (1978) enables one to determine the nitrosamine inhibiting effect of said compounds. A further method which can be used is that described by Walters et al., Z. Lebensm. Unter-Forsch. 162, 377 (1976) which makes use of model systems to determine nitrosamine inhibition of a given compound.

The present invention is illustrated by the following Examples. It should, however, be understood that the invention is not limited to the specific details of these examples, variations of which are possible as indicated by the above disclosure.

EXAMPLE 1

5-Keto-L-Ascorbic Acid-5,5-Dimethyl Ketal Sodium Salt

To a solution of methyl 2,5-diketogluconate-5,5-dimethyl ketal (2.52 g., 10.0 mmoles) in anhydrous methanol (10 ml.) at 0° C. under a nitrogen atmosphere was added sodium methoxide (9.0 ml. of 1.0 N) in methanol (10 ml.). The mixture was stirred at room temperature overnight and the resulting gel-like crystals filtered, washed with anhydrous methanol and then dried in vacuo (room temperature) for three days. The resulting white, friable powder hydrated upon standing in the air to give 1.1 g. (42%) of the monohydrate of the title product.

M.P. 165°–167° C. (dec.).

IR (KBr): 3413 (s, OH), 1733 (s), 1597 (s) cm$^{-1}$.

$^1$H NMR (60 MHz) $\delta_{D_2O}^{TMS}$ (ppm): 4.60 (s, 1,

3.68 (s, 2, —CH$_2$—OH), 3.35 [s, 6, (CH$_3$O$_2$)].

$^{13}$C NMR (D$_2$O) (ppm): 176.5 (s), 176.1 (s), 113.2 (s), 100.5 (s), 77.5 (d), 59.6 (t), 49.8 and 49.3 (q).

UV (H$_2$O): $\lambda_{max}$ 269 m$\mu$ ($\epsilon$=9.01×10$^3$).

Analysis: Calc'd. for C$_8$H$_{11}$ONa.H$_2$O: C, 36.93; H, 5.03. Found: C, 37.23; H, 4.37.

EXAMPLE 2

5-Keto-L-Ascorbic Acid-5,5-Dimethyl Ketal

To a solution of methyl 2,5-diketogluconate-5,5-dimethyl ketal (11.46 g., 45.5 mmols) in anhydrous methanol (500 ml.) was added sodium bicarbonate (7.65 g., 91 mmols). The mixture was heated at reflux under nitrogen for five hours and then stirred at ambient temperature overnight. The jelled reaction mixture of the sodium salt of the title compound was broken up and 75 ml. of Amberlite 15 resin (a sulfonic acid cation exchange resin available from Rohm and Haas Co.), acid form, previously washed with methanol, was added. The mixture was stirred until a clear solution formed (about one hour) and the resin then removed by filtration. The filtrate was evaporated in vacuo to an oil and then refrigerated overnight. The crystalline mass which formed was ground and vacuum dried. Yield, 9.70 g. (96.9%) of product which was homogeneous by thin layer chromatography (silica gel; n-butanol:acetic acid:-water; 2:1:1).

M.P. 123.5°–124.0° C.; $[\alpha]_D^{25}$ −23.3° (c 0.54, H$_2$O).

U.V. (CH$_3$OH): $\lambda_{max}$ 250 m$\mu$ ($\epsilon$=5.34×10$^3$).

$^1$H NMR (60 MHz) $\delta_{DMSO-d_6}^{TMS}$ (ppm): 4.84 (s, 1,

3.47 (s, 2, —CH$_2$—OH); 3.25 [s, 6, (CH$_3$O)$_2$].

$^{13}$C NMR (D$_2$O) (ppm): 172.7 (s), 156.0 (s), 118.8 (s), 101.6 (s), 74.8 (d), 59.4 (t), 50.4 and 49.9 (q).

IR (KBr) cm$^{-1}$ 1767 (s), 1658 (s).

Anal. Calc'd. for C$_8$H$_{12}$O$_7$: C, 43.64; H, 5.49. Found: C, 43.79; H, 5.44.

EXAMPLE 3

5-Keto-L-Ascorbic Acid

To 5-keto-L-ascorbic acid-5,5-dimethyl ketal (1.0 g., 4.54 mmols) was added trifluoroacetic acid (19 ml.) and water (1 ml.) at ambient temperature. The mixture was stirred for 30 minutes and the trifluoroacetic acid and water removed under high vacuum to give a light yellow oil. Thin layer chromatography in the system silica gel, butanol:acetic acid:water (2:1:1) showed the oil to be homogeneous. The oil was taken up in water (10 ml.) the solution treated with activated charcoal (200 mg.) and filtered. Refrigeration of the filtrate for 3 days afforded a crystalline material which was removed by filtration and dried in air. Yield=568 mg., 65% as monohydrate.

M.P. 135°-138° C. (dec.).
$[\alpha]_D^{25}$ 0.0° (c 1, H$_2$O).
U.V. (H$_2$O, pH 2.65): $\lambda_{max}$ 242, A=0.82, 300 (A=0.10).
$^1$H NMR (60 MHz) $\delta_{DMSO-d_6}^{TMS}$ (ppm) 4.58 (s, 1), 3.63 (A B quartet, 2, J=11.8 Hz).
$^1$H NMR (60 MHz) $\delta_{D_2O}^{TMS}$ (ppm): 3.45 (s, 2), 4.27 (s, 1).
$^{13}$C NMR (DMSO-d$_6$) (ppm): 169.7 (s), 152.0 (s), 119.0 (s), 92.3 (s), 76.7 (d), 76.3 (d), 65.8 (t), 62.1 (t).

EXAMPLE 4

L-Ascorbic Acid (by Sodium Cyanoborohydride Reduction)

5-Keto-L-ascorbic acid-dimethyl ketal (475 mg., 2.16 mmols) was dissolved in water (1 ml.), cooled to 0° C. and trifluoroacetic acid (19 ml., previously cooled to 0° C.) added slowly (pH ~2.5). The reaction mixture was stirred at 0° C. for one hour, and at 25° C. for 30 minutes after which the solvent was removed under high vacuum at below room temperature. The residue was taken up in water (30 ml.) and treated with 542 mg. (32 mmols) sodium cyanoborohydride. The mixture was stirred at 25° C. for 2 hours and excess Dowex 50, a sulfonic acid cation exchange resin (20 ml., acid form, available from the Dow Chemical Co.) was added to decompose the excess cyanoborohydride. The resin was removed by filtration, and the methanol removed by distillation. The residue was re-dissolved in methanol (20 ml.) and the methanol removed by distillation. This step was repeated two more times to affect removal of boric acid residues. The final solid isolated comprised 388 mg. (100%) of an iodine reducing material, shown by thin-layer chromatographic analysis (silica gel, n-butanol:acetic acid:water, 2:1:1) to be a mixture of ascorbic and erythorbic acids. A portion of the residue was per-trimethylsilylated with trimethylsilylchloride in pyridine according to the procedure of Bacon et al., J. Lab. and Clin. Med., 73, 1030 (1969). The procedure comprised dissolving a 5-20 mg. sample of the residue in a mixture of N-trimethylsilylimidazole, N,O-bis-(trimethylsilyl)acetamide and trimethylchlorosilane (3:2:2 v/v) in pyridine (available from Pierce Chemical Co., as Tri-Sil TBT). The reaction mixture is allowed to stand for 15 minutes and is then injected directly onto the GLPC column. Gas liquid phase chromatographic (GLPC) analysis of the pertrimethylsilylated derivative showed a mixture of erythorbic acid and ascorbic acid in a ratio of 26:74.

The GLPC analysis was accomplished using a 5', ⅛" O.D. column packed with 3% OV-210 on Chromasorb WHP, 100/120 mesh, isothermally at a temperature of 135° C. and a carrier gas flow rate of 30 ml./minute. OV-210 is a silicon oil polymer containing 50% 3,3,3-trifluoromethyl groups and is marketed by Analabs Inc., a subsidiary of New England Nuclear, 80 Republic Drive, North Haven, CT 06473. Chromasorb WHP is a registered trademark of the Johns-Manville Co., 22 E. 40th St., New York, NY 10016 for a diatomite support which is acid washed and dimethylchlorosilane treated.

EXAMPLE 5

L-Ascorbic Acid (by Zinc Cyanoborohydride Reduction)

5-Keto-L-ascorbic acid-5,5-dimethyl ketal (195 mg., 0.887 mmols) was dissolved in trifluoroacetic acid-water (5.0 ml. of 95:5) and stirred at room temperature (pH ~2) under nitrogen for 15 minutes. Removal of solvent under high vacuum at below room temperature afforded a foam residue which was re-dissolved in water (5.0 ml.). After the sequential addition of anhydrous zinc chloride (60.4 mg., 0.443 mmols) and sodium cyanoborohydride (371.6 mg., 5.913 mmols) the solution was stirred at room temperature under nitrogen for 16 hours. Analysis of the reaction mixture by thin layer chromatography (silica gel; n-butanol:acetic acid:water; 2:1:1) showed the presence of L-ascorbic acid. The reaction mixture was stirred with 15 ml. of Dowex 50 ion exchange resin (sulfonic acid form) for 3 hours after which the resin was removed by filtration and the filtrate stripped in vacuo to a white solid residue. The residue was placed in a 50 ml. round-bottom flask charged with methanol (25 ml.) and fitted with a Soxhlet extractor containing 10 ml. of Ag 1-×8 resin (a quaternary ammonium ion exchange resin, hydroxide form, available from Rohm and Haas Company). The solution was heated at reflux for 5 hours to absorb boric acid residues on the ion exchange resin, cooled, and the methanol removed by rotatory evaporation. The residue was derivatized with trimethylsilyl chloride in pyridine according to the procedure of Example 4. GLPC analysis of the derivatized reaction mixture (5', 3% OV-210 column at 135° C. and flow rate of 30 ml./min.) showed the presence of ascorbic acid and erythorbic acids in a ratio of 2:1.

EXAMPLE 6

5-Keto-L-Ascorbic Acid Dimethyl Ketal Salts

The procedure of Example 1 is followed but with the modifications in reaction conditions noted below to afford, depending upon the base used, the alkali metal or alkaline earth metal salts of 5-keto-L-ascorbic acid dimethyl ketal.

| Solvent | Base | Equivalent Moles DMG*/Base | T °C. | Time (Hours) |
|---|---|---|---|---|
| CH$_3$OH | NaOCH$_3$ | 2:1 | 22 | 18 |
| CH$_3$OH | NaOCH$_3$ | 1:2 | 25 | 20 |
| CH$_3$OH | KOCH$_3$ | 1:1 | 22 | 20 |
| C$_2$H$_5$OH | NaOC$_2$H$_5$ | 1:1 | 20 | 24 |
| C$_4$H$_9$OH | KOC$_4$H$_9$ | 1.5:1 | 25 | 20 |
| C$_4$H$_9$OH | NaOCH$_3$ | 1:1 | 30 | 18 |
| isopropanol | KO—i-C$_3$H$_7$ | 1:1.5 | 22 | 22 |
| CH$_3$OH | KHCO$_3$ | 1:2 | reflux | 5 |
| CH$_3$OH | Na$_2$CO$_3$ | 1:2 | reflux | 6 |
| CH$_3$OH | NaOH | 1:1 | 50 | 5 |
| CH$_3$OH | NaH | 2:1 | 20 | 18 |

-continued

| Solvent | Base | Equivalent Moles DMG*/Base | T °C. | Time (Hours) |
|---|---|---|---|---|
| H₂O | K₂CO₃ | 1:2 | reflux | 4 |
| H₂O | KHCO₃ | 2:1 | 80 | 5 |
| CH₃OH—H₂O(1:1) | KOH | 1:2 | 25 | 24 |
| CH₃OH—H₂O(95:5) | NaHCO₃ | 1:2 | reflux | 5 |
| CH₃OH | KOCH₃ | 1:1 | 20 | 18 |
| H₂O | Ca(OH)₂ | 1:1.5 | 75 | 10 |
| H₂O | CaCO₃ | 1:1 | reflux | 18 |
| H₂O | Ba(OH)₂ | 1:1 | 80 | 8 |
| H₂O | BaCO₃ | 1:1.5 | reflux | 18 |
| CH₃OH | Ca(OCH₃)₂ | 1:1 | reflux | 6 |
| CH₃OH | Sr(OH)₂ | 1:2 | reflux | 5 |
| H₂O | Sr(HCO₃)₂ | 1:1 | reflux | 6 |
| H₂O | LiOH | 1:1 | 60 | 6 |
| C₂H₅OH | LiOH | 1:1.2 | reflux | 5 |
| CH₃OH | Mg(OH)₂ | 1:1 | reflux | 6 |

*DMG = methyl 2,5-diketogluconate-5,5-dimethyl ketal.

EXAMPLE 7

5-Keto-L-Ascorbic Acid Dimethyl Ketal

The procedure of Example 2 is repeated but using the following acids for neutralization of the sodium salt:

Dowex 50 (sulfonic acid cation exchange resin, acid form, available from the Dow Chemical Co.).

Amberlite IRC-50 (carboxylic acid cation exchange resin, acid form, Rohm and Haas Co.).

H₂SO₄.

HCl.

Methanesulfonic acid.

EXAMPLE 8

5-Keto-L-Ascorbic Acid

The procedure of Example 3 is repeated but substituting the acids listed below for trifluoroacetic acid to give the title compound.

Acid
trichloroacetic
hydrochloric
hydrofluoric
sulfonic
methanesulfonic acid
p-toluenesulfonic acid.

EXAMPLE 9

5-Keto-L-Ascorbic Acid Sodium Salt

The procedure of Example 3 is repeated but the aqueous solution of 5-keto-L-ascorbic acid obtained is neutralized with dilute (1 N) sodium hydroxide to give the sodium salt which is recovered by lyophilization.

In like manner the potassium, lithium, calcium, barium, magnesium and strontium salts are prepared.

EXAMPLE 10

5-Keto-L-Ascorbic Acid-5,5-Dimethyl Ketal

To a solution of methyl 2,5-diketogluconate-5,5-dimethyl ketal (10.0 g., 39.7 mmols) in anhydrous methanol (100 ml.) was added sodium bicarbonate (3.36 g., 40.0 mmol). The mixture was stirred vigorously at reflux for 4 hours, cooled to 40° C. and concentrated sulfuric acid (1.08 ml., 20 mmol) added dropwise to the stirred solution. On cooling to ambient temperature, ether (50 ml.) was added and the precipitated sodium sulfate removed by filtration.

Workup as in Example 2 afforded 5-keto-L-ascorbic acid-5,5-dimethyl ketal in 89% yield by iodine titration.

EXAMPLE 11

L-Ascorbic Acid (by sodium borohydride reduction in trifluoroacetic acid)

To a rapidly stirring solution of 5-keto-L-ascorbic acid-5,5-dimethyl ketal (3.72 g., 16.9 mmols) in 50 ml. of trifluoroacetic acid at ice bath temperature was added sodium borohydride pellets (0.750 g., 19.8 mmol). The mixture was stirred at 0° C. for 3 hours under nitrogen, the trifluoroacetic acid removed by rototory evaporation and the residue taken up in 50 ml. of methanol. The methanol was treated with 1.65 ml. of concentrated HCl and the precipitated sodium chloride removed by filtration. The filtrate was concentrated by rototory evaporation with subsequent addition of methanol three times to affect removal of trimethylborate, finally affording a tan solid shown by TLC (silica gel, ethyl acetate-ethanol-water, 5-3-2) to be a mixture of L-ascorbic acid and D-erythorbic acid. A portion of the solid (10 mg.) was per-trimethyl silylated with Tri-Sil TBT as in Example 4. GLPC analysis of the per-trimethylsilylated derivative showed a mixture of D-erythorbic and L-ascorbic acids in a ratio of 23:77.

The crude solid was chromatographed on silica gel (180 g.). Elution with ethyl acetate-ethanol-water (5-3-1) afforded 2.64 g. (76%) of L-ascorbic acid (by TLC and GLPC analysis according to the procedures described above). It was shown to be 95% pure by iodine titration. A sample was crystallized from methanol-ethyl acetate, 1—1.

M.P. 187°–190° C.

$[\alpha]_D^{23}$ 18.0° (C=1, H₂O).

¹H NMR (D₂O) δ 4.75 (d, 1); 3.76 (multiplet, 1); 3.49 (multiplet, 2).

I claim:

1. A process for making L-ascorbic acid which comprises reacting 5-keto-L-ascorbic acid-5,5-dimethyl ketal with sodium borohydride in a trifluoroacetic acid medium.

* * * * *